United States Patent
Gottenbos et al.

(10) Patent No.: US 8,696,353 B2
(45) Date of Patent: Apr. 15, 2014

(54) ANTIMICROBIAL FILLED CAPSULES IN AN ULTRASOUND FIELD FOR TREATMENT OF DENTAL BIOFILM

(75) Inventors: Bart Gottenbos, Budel (NL); Marcel Rene Bohmer, Eindhoven (NL); Jozef Johannes Maria Janssen, Herten (NL)

(73) Assignee: Koninklijke Philips N.V., Eindhoven (NL)

( * ) Notice: Subject to any disclaimer, the term of this patent is extended or adjusted under 35 U.S.C. 154(b) by 755 days.

(21) Appl. No.: 12/808,254

(22) PCT Filed: Dec. 9, 2008

(86) PCT No.: PCT/IB2008/055167
§ 371 (c)(1),
(2), (4) Date: Jun. 15, 2010

(87) PCT Pub. No.: WO2009/077921
PCT Pub. Date: Jun. 25, 2009

(65) Prior Publication Data
US 2010/0269281 A1   Oct. 28, 2010

Related U.S. Application Data

(60) Provisional application No. 61/014,495, filed on Dec. 18, 2007.

(51) Int. Cl.
*A61C 17/00* (2006.01)
*A61C 17/02* (2006.01)
(52) U.S. Cl.
USPC .......................................................... 433/80
(58) Field of Classification Search
USPC ...................... 433/80, 86, 119; 424/450, 489, 424/498–502; 600/437–472, 561; 15/22.1, 15/24, 29; 601/2; 604/23, 24, 26
See application file for complete search history.

(56) References Cited

U.S. PATENT DOCUMENTS

| 4,116,239 | A | * | 9/1978 | Ewen ........................ 128/200.16 |
| 4,148,309 | A | | 4/1979 | Reibel |
| 4,980,150 | A | | 12/1990 | Keith |
| 5,378,153 | A | | 1/1995 | Giuliani et al. |
| 6,145,516 | A | | 11/2000 | Guay et al. |
| 6,174,164 | B1 | | 1/2001 | Masjedi |
| 6,193,951 | B1 | | 2/2001 | Ottoboni et al. |
| 6,348,186 | B1 | * | 2/2002 | Sutton et al. ................ 424/9.52 |
| 6,896,659 | B2 | * | 5/2005 | Conston et al. ............. 600/458 |
| 2001/0025145 | A1 | * | 9/2001 | Tickner et al. ............. 600/458 |

(Continued)

FOREIGN PATENT DOCUMENTS

| DE | 4340598 A1 | 6/1995 |
| JP | 20018736 A | 1/2001 |

(Continued)

*Primary Examiner* — Robyn Doan
*Assistant Examiner* — Matthew Nelson

(57) ABSTRACT

An appliance and corresponding method for delivering antimicrobial agents to the vicinity of dental biofilm and for killing bacteria therein includes a system (18, 20, 24) for delivering polymeric capsules containing gas bubbles and an antimicrobial agent. A source of ultrasonic energy (18) is provided for moving the capsules toward the biofilm, the ultrasonic energy having sufficient intensity for thereafter bursting the capsules, in the vicinity of the biofilm, releasing the gas bubbles and the agent. The gas bubbles vibrate within the ultrasound field, disrupting the biofilm, so that the released agent can act effectively against the bacteria in the disrupted biofilm.

18 Claims, 2 Drawing Sheets

(56) References Cited

U.S. PATENT DOCUMENTS

| | | |
|---|---|---|
| 2005/0075621 A1 | 4/2005 | Rontal |
| 2005/0241668 A1 | 11/2005 | Trampuz et al. |
| 2006/0191086 A1 | 8/2006 | Mourad et al. |
| 2007/0054978 A1* | 3/2007 | Futigami et al. ............. 523/116 |
| 2008/0089912 A1* | 4/2008 | DiMauro ...................... 424/400 |
| 2009/0221902 A1* | 9/2009 | Myhr .......................... 600/411 |
| 2010/0221190 A1* | 9/2010 | Bohmer et al. ............. 424/9.52 |
| 2011/0159461 A1* | 6/2011 | Mourad et al. ................ 433/216 |

FOREIGN PATENT DOCUMENTS

| | | |
|---|---|---|
| JP | 200616392 A | 1/2006 |
| WO | 2004032889 A1 | 4/2004 |
| WO | 2007060644 A3 | 5/2007 |
| WO | 2007064519 A1 | 6/2007 |
| WO | WO 2007060644 A3 * | 9/2007 |

* cited by examiner

ANTIMICROBIAL FILLED CAPSULES IN AN ULTRASOUND FIELD FOR TREATMENT OF DENTAL BIOFILM

This invention relates generally to the killing of bacteria present in biofilms on dental surfaces, and more specifically concerns the delivery of antimicrobial or other agents to the dental biofilm to kill bacteria therein.

Dental biofilm, occurring on human teeth, comprises various layers of bacteria and other organisms embedded in what is referred to as a slime matrix. This includes dental plaque, which is important to control in order to prevent dental decay. This is typically done by daily brushing, flossing and in some cases by the use of antimicrobial rinses. The use of antimicrobial rinses, however, is often not particularly effective, due to the characteristics of the biofilm/slime matrix. The bacterial microorganisms can be protected from the antimicrobial agents by various conditions, including blockage of the agents by the slime matrix itself, or the slime matrix could contain enzymes which break down the agents. Further, part of the biofilm population may be alive but not active, and hence not particularly susceptible to the antimicrobial agents. Antibiotics could be used against the dental bacteria, but must be prescribed, and further, are not suitable for everyday use.

In addition, many available antimicrobial agents have significant disadvantages, including staining of teeth and/or altering the taste capability of the user. Those which do not have significant side effects are often not particularly effective against dental bacteria in biofilms. Further, users often do not comply with required time duration and/or advisable methods of use for the agents to be effective.

Accordingly, a system and/or method for effective treatment of dental biofilms using conventional over-the-counter antimicrobial agents is desirable.

Accordingly, an appliance and corresponding method is disclosed herein for delivering anti-bacterial agents to the vicinity of dental biofilm for killing the bacteria therein, comprising: a system for delivering polymeric capsules containing gas bubbles and a bacteria-killing agent; and a source of ultrasonic energy for moving the capsules toward the dental biofilm and for thereafter bursting the capsules in the vicinity of the biofilm, releasing the gas bubbles and the bacteria-killing agent, wherein the ultrasound energy has a frequency which is related to the size of the gas bubbles such that the released gas bubbles vibrate in the ultrasound field in the vicinity of or against the biofilm, disrupting the biofilm to the extent that the released anti-bacterial agent acts effectively to kill the bacteria in the disrupted dental biofilm.

Figure 1:
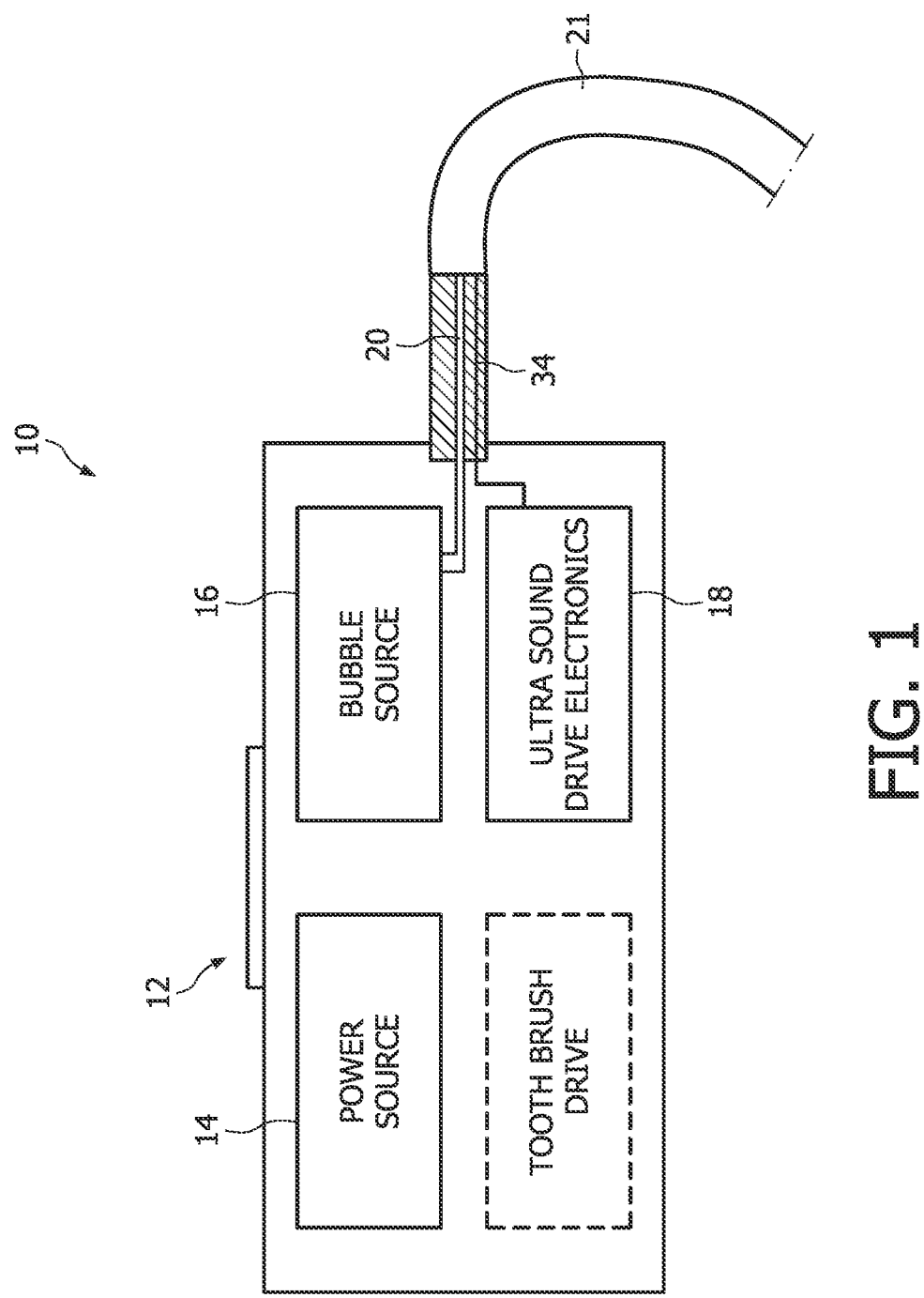
FIG. 1 is a simplified drawing showing a system which delivers antimicrobial agents to dental biofilm in the mouth.

FIG. 1 shows a dental appliance which is effective in delivering an antimicrobial agent to the vicinity of dental biofilm for killing of the bacteria contained therein. In general, the appliance 10 uses polymeric capsules. The polymeric capsules contain gas bubbles and an antimicrobial agent which is capable of killing bacteria commonly found in dental biofilm. While this description primarily concerns antimicrobial agents as the bacteria-killing agent, since they are generally effective and safe for daily use, it should be understood that the agent could be other types of bacteria-killing compositions, including antibiotics which can be used to treat dental biofilm or other conditions/infections in the mouth or elsewhere in the body.

The polymeric capsules are directed out of an applicator portion of the appliance, in the direction of the dental biofilm, by an ultrasound field created by an ultrasound transducer within the appliance. At a selected ultrasound intensity, the capsules in the vicinity of the biofilm will break under the effect of the ultrasound, releasing the antimicrobial agent and the gas bubbles. The size of the gas bubbles matches the frequency of the ultrasound signal, so that the bubbles in the ultrasound field begin to vibrate, reach a maximum amplitude of vibration and then impact and disrupt the biofilm, resulting in the dental bacteria becoming generally free from the biofilm/slime matrix, i.e. the bacteria is now in the plantonic state. This allows the antimicrobial agent released from the capsule to be effective in killing the bacteria.

In more detail, appliance 10 will typically include a console portion 12 which will typically be placed on a cabinet surface of some kind where the appliance is to be used. The console includes a power source 14, such as a battery, for the appliance. Also within the handle is a capsule-containing source 16 and an ultrasound drive system 18. The capsules are directed along a line 20 in a connecting portion 21 of the appliance to an applicator 23 and out through a nozzle 24 in an applicator head 25, as shown in FIG. 1, or nozzles 26-26 in a brushhead 27 in FIG. 2. Brushhead 27 includes a set of conventional toothbrush bristles 29. The appliance can also include a brushhead drive system 31 for moving the brushhead in a desired pattern.

Figure 2:
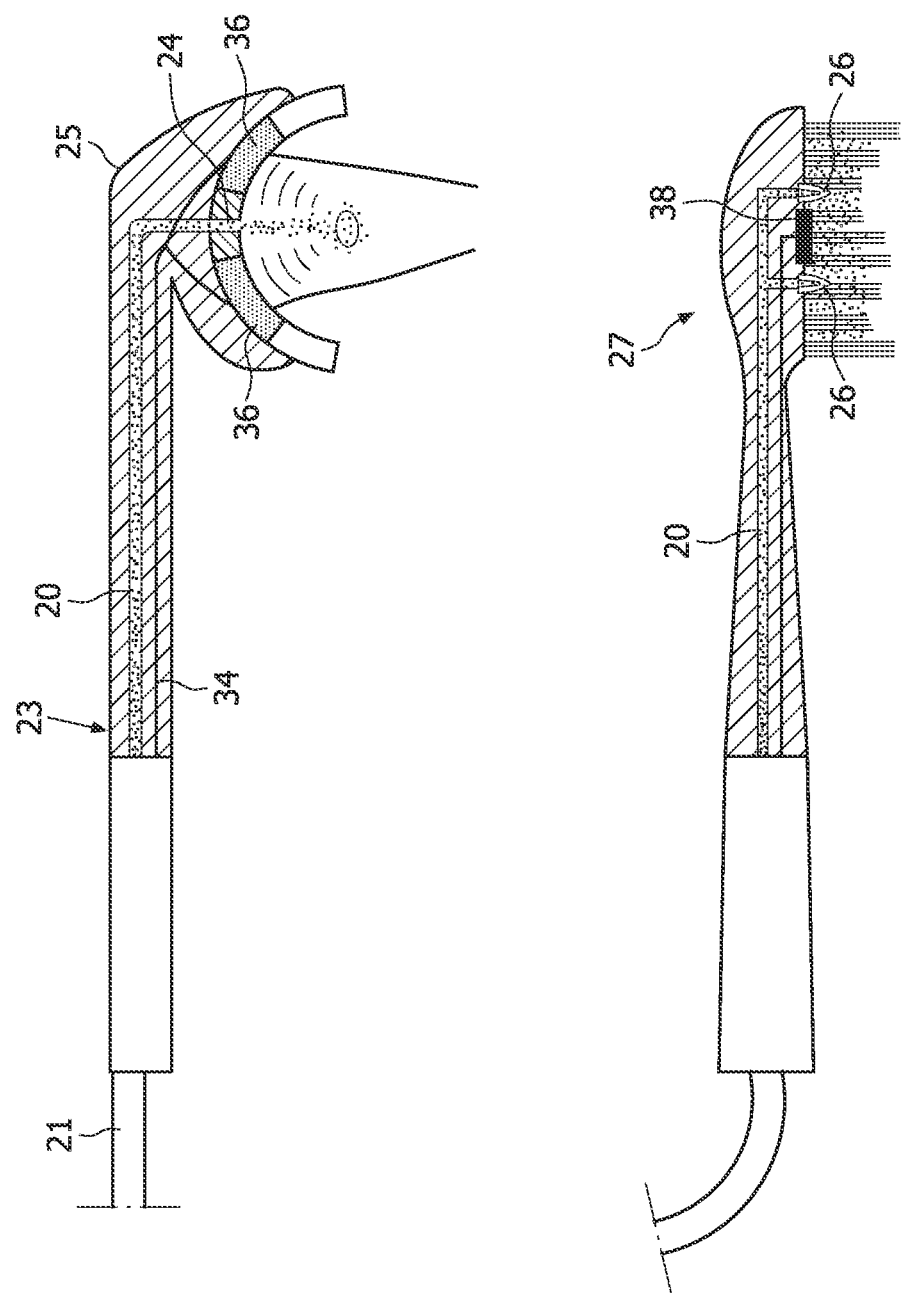
FIG. 2 is a simplified diagram showing an embodiment similar to claim 1, but including bristles on an applicator portion thereof which can be used to mechanically brush the teeth as well.

An ultrasound signal from ultrasound drive source 18 is applied along a line 34 to transducers 36-36 in applicator head 25 or transducer 38 in brushhead 27. It should be understood that the applicator arrangements shown in FIGS. 1 and 2 are examples only, and various configurations of applicators and brushheads can be used. Each applicator embodiment, however, will have within it an outlet, typically a nozzle of some kind, for the capsules and an ultrasound transducer. Also, while console 12 is shown as a unit separate from the applicator, it may be possible to combine the functions of console 12 and the applicator in a unitary, hand-held appliance.

It should also be understood that in an alternative embodiment, the polymeric capsules could also be entrained into a dentifrice-like formulation that is applied to the appliance by the user. Such a dentifrice could be similar to conventional dentifrices. The appliance could then direct the dentifrice towards the surface of the teeth, for example by the oscillation of a plurality of bristles, after which the ultrasound signal is applied, leading to the effects described above.

The fabrication of the capsules is done separately from the appliance in a process which is widely known in the art, and hence is not described herein in detail. Briefly, the polymeric capsules are produced using a solution of polymer dichloromethane with antimicrobial agents dissolved therein. The dichloromethane is then evaporated, leaving the agent and gas bubbles surrounded by a polymer shell. The polymer shell itself can comprise a variety of compositions, but generally includes a polyactic acid with fluorinated end groups, which is biodegradable. The capsules with the gas bubbles and the antimicrobial agents therein are contained in a formulation which could be similar to a dentifrice and are directed to the applicator.

In some cases, surface chemicals are added to the capsules which results in the capsules adhering to the dental biofilm surface. In one particular arrangement, capsules are given a positive surface charge, such as by amine or ammonium groups. Since biofilms have a negative surface charge, the capsules will bind to the biofilms by electrostatic interaction.

In the embodiment shown, the size of the capsules will vary, but will generally be in the range of 1-80 micrometers.

The size of the gas bubbles will also vary, from 1 micrometer to 50 micrometers, corresponding to an ultrasound frequency range of 100 kHz to 4 MHz. In one specific example, for a 1 MHz ultrasound frequency, the gas bubble size will be 6-8 microns. The agents for killing the bacteria, as indicated above, will be primarily over-the-counter antimicrobial agents, which for example can include compositions like various mouth rinses, such as Triclosan or thymol, eucalyptol, menthol and methyl salicylate. Other antiseptic hydrophobic agents can also be used. Different antibiotics can also be used, as discussed above, depending upon the particular application, but not for daily biofilm treatment.

The gas bubbles can be a variety of gases, including air. As indicated above, the most important aspect is the size of the gas bubbles, which should have a resonant frequency close to the ultrasound frequency. When the bubble is resonated, it achieves its maximum amplitude of vibration and can produce the most effective disruption of the biofilm structure. Further, the oscillating bubbles will cause a microstreaming effect, which assists in disrupting the biofilm.

The capsules can be formulated as a fluid, like a conventional mouthwash, or as a more viscous substance, similar to a dentifrice. The concentration of the capsules can be similar to conventional antimicrobial agent formulations, or they could be significantly lower, because the capsules, with the agent, become highly concentrated together on the biofilm, in response to the ultrasound streaming effect.

As indicated above, the ultrasound/transducer creates a field which extends to the biofilm from the applicator. The intensity of the ultrasound can be varied to enhance the effectiveness of the system. For instance, a low-intensity field can be used to concentrate the capsules on the biofilm surface. The slight oscillation of the capsules caused by the low-intensity field will attract the capsules to each other and to the surface by a microstreaming effect. The ultrasound intensity may thereafter be increased above the threshold where the capsules break, producing a very high concentration of the antimicrobial agent right at the biofilm, as well as the simultaneous release of the gas bubbles. The gas bubbles are then resonated by the ultrasound, leading to disruption of the biofilm, so that the antimicrobial agent has a significant effect.

In another approach, the intensity of the ultrasound could be just at the threshold for breaking the capsules, releasing only a small number of bubbles with a short ultrasound pulse (approximately 1-5 ultrasound cycles), followed by a series of lower-energy ultrasound pulse cycles, which agitate the released bubbles to cause biofilm disruption, until the free (released) bubbles are dissolved. The process is then repeated until all the capsules have been broken.

In still another approach, a variety of capsule thicknesses can be used, each having different threshold intensities for breaking. Gradually increasing the intensity of the ultrasound pulses will produce a sequence of capsule breakage and subsequent vibration of the gas bubbles therein, disrupting the biofilm in successive steps.

Hence, a system for effectively delivering antimicrobial agents to a dental biofilm, disrupting the biofilm with vibrating gas bubbles and then killing of the bacteria therein has been disclosed, as well as a sequence of steps for accomplishing the biofilm disruption and killing of the bacteria therein by delivering and breaking a plurality of capsules containing gas bubbles and an antimicrobial agent.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. An appliance system for delivering a bacteria-killing agent to the vicinity of dental biofilm for killing the bacteria there, the appliance system comprising:
   a polymeric capsule-containing source in the appliance system having polymeric capsules containing gas bubbles and a bacteria-killing agent therein;
   a system in the appliance system for delivering the polymeric capsules from the polymeric capsule-containing source in the direction of the biofilm; and
   a source of ultrasonic energy in the appliance system for moving the capsules toward the dental biofilm, the ultrasound energy having sufficient intensity for thereafter bursting the capsules in the vicinity of the biofilm, releasing the gas bubbles and the bacteria-killing agent, wherein the ultrasound has a frequency which is related to the size of the gas bubbles such that the released gas bubbles vibrate in the ultrasound field in the vicinity of or against the biofilm, disrupting the biofilm to the extent that the released bacteria-killing agent acts effectively to kill the bacteria in the disrupted dental biofilm.

2. The appliance system of claim 1, wherein the gas bubbles have such a size that they resonate at maximum amplitude at the frequency of the ultrasound signal.

3. The appliance system of claim 1, wherein the range of size of the gas bubbles is 1-50 microns.

4. The appliance system of claim 1, including an applicator (25) without bristles.

5. The appliance system of claim 1, including an applicator (27) which includes bristles for brushing the teeth.

6. The appliance system of claim 1, including a system (18) for controlling the source of ultrasound energy so as to produce a lower intensity ultrasound pulse to concentrate the capsules on the biofilm, followed by a plurality of higher intensity ultrasound pulses, sufficient to burst the capsules.

7. The appliance system of claim 1, including a system (18) for controlling the source of ultrasound energy, including producing a repeating sequence comprising a short ultrasound pulse to break a few capsules, followed by a plurality of lower energy ultrasound pulses which vibrate the gas bubbles to disrupt the biofilm until the gas bubbles are dissolved.

8. The appliance system of claim 1, wherein the capsules have different threshold ultrasound signal intensities at which they break, and wherein the ultrasound intensity is gradually increased, breaking the capsules in a sequence.

9. The appliance system of claim 1, wherein the capsules include a physical characteristic which tends to bind the capsules to the biofilm.

10. The appliance system of claim 9, wherein the physical characteristic is a positive charge on the capsule.

11. A method for delivering anti-bacterial agents to the vicinity of dental biofilm and for killing bacteria therein, comprising the steps of:
    delivering a plurality of polymeric capsules containing gas bubbles and an antibacterial agent in the direction of the biofilm;
    bursting the capsules by ultrasound action having sufficient intensity to do so, releasing the gas bubbles and the antibacterial agent in the vicinity of the dental biofilm; and
    vibrating the gas bubbles by the ultrasound action so that the gas bubbles disrupt the dental biofilm sufficiently to enable killing of the bacteria therein by the antibacterial agent.

12. The method of claim 11, wherein the capsules are delivered by ultrasound action.

13. The method of claim 11, wherein the size of the gas bubbles is such that the gas bubbles resonate at maximum amplitude at the frequency of the ultrasound signal.

14. The method of claim 13, wherein the size of the bubbles is within the range of 1-50 microns.

15. The method of claim 12, wherein the ultrasound is provided in a series of pulses, including a sequence of a high intensity pulse or pulses sufficient to break the capsules, followed by a plurality of lower intensity pulses for vibrating the gas bubbles.

16. The method of claim 12, wherein the capsules have different ultrasound intensities at which they break, and wherein the ultrasound energy is gradually increased in intensity to break the capsules in a sequence.

17. The method of claim 12, wherein the agent is an antimicrobial agent.

18. The method of claim 12, wherein the capsule is positively charged so as to adhere to the biofilm layer.

* * * * *